(12) United States Patent
Gu et al.

(10) Patent No.: US 10,590,622 B2
(45) Date of Patent: Mar. 17, 2020

(54) DROP HAMMER HEIGHT ADJUSTING DEVICE FOR HIGH STRAIN DETECTION OF PILE FOUNDATION

(71) Applicant: Kunshan Construct Engineering Quality Testing Center, Kunshan (CN)

(72) Inventors: Sheng Gu, Kunshan (CN); Pengfei Wang, Kunshan (CN); Junhua Cai, Kunshan (CN); Yulong Wu, Kunshan (CN)

(73) Assignee: KUNSHAN CONSTRUCT ENGINEERING QUALITY TESTING CENTER, Kunshan (CN)

( * ) Notice: Subject to any disclaimer, the term of this patent is extended or adjusted under 35 U.S.C. 154(b) by 186 days.

(21) Appl. No.: 15/751,263

(22) PCT Filed: Nov. 8, 2016

(86) PCT No.: PCT/CN2016/105034
§ 371 (c)(1),
(2) Date: Feb. 8, 2018

(87) PCT Pub. No.: WO2018/014466
PCT Pub. Date: Jan. 25, 2018

(65) Prior Publication Data
US 2018/0238013 A1    Aug. 23, 2018

(30) Foreign Application Priority Data

Jul. 18, 2016  (CN) .......................... 2016 1 0564885

(51) Int. Cl.
*E02D 33/00*    (2006.01)
*G01N 3/30*    (2006.01)

(52) U.S. Cl.
CPC ............... *E02D 33/00* (2013.01); *G01N 3/30* (2013.01); *G01N 2203/0033* (2013.01); *G01N 2203/0039* (2013.01); *G01N 2203/0075* (2013.01)

(58) Field of Classification Search
CPC .. G01N 3/303; G01N 3/30; G01N 2203/0033; G01N 2203/0623; G01M 7/08
(Continued)

(56) References Cited

U.S. PATENT DOCUMENTS 3,115,774 A * 12/1963 Kolb ....................... E21B 12/02
73/152.03
3,190,110 A * 6/1965 Craycraft ............... G01N 3/303
73/12.06
(Continued)

FOREIGN PATENT DOCUMENTS

CN     203129118 U    8/2013
CN     204252175    *    4/2015    ............. E02D 33/00
(Continued)

*Primary Examiner* — Clayton E. LaBalle
*Assistant Examiner* — Kevin C Butler
(74) *Attorney, Agent, or Firm* — SZDC Law PC

(57) ABSTRACT

The invention provides a drop hammer height adjusting device for high strain detection of a pile foundation, the device comprises: a cross beam support frame, an avoiding hole is opened in the middle of the surface of the cross beam support; a track extending through the avoiding hole, a tooth group is arranged on each of two surfaces of the track bar, and abutting sliding blocks are further arranged at two sides of the track bar. The abutting sliding block is cooperated with the tooth group to limit the position of the track bar. The invention overcomes the significant disadvantages of the existing detection devices, the efficiency of obtaining qualified test signals is improved by the rapid and accurate height
(Continued)

adjustment and test, and the precision and efficiency of high strain detection of a foundation pile are greatly improved.

9 Claims, 4 Drawing Sheets

(58) Field of Classification Search
USPC .................................................. 73/12.06
See application file for complete search history.

(56) References Cited

U.S. PATENT DOCUMENTS

| | | | | | |
|---|---|---|---|---|---|
| 3,200,599 | A | * | 8/1965 | Phares | E02D 5/36 405/241 |
| 3,470,701 | A | * | 10/1969 | Turzillo | E02D 1/022 405/233 |
| 3,498,388 | A | * | 3/1970 | Jovis | E02D 13/06 173/2 |
| 3,824,797 | A | * | 7/1974 | Wisotsky | E02D 7/00 405/228 |
| 3,905,428 | A | * | 9/1975 | Nishimura | E02D 7/125 173/128 |
| 3,931,729 | A | * | 1/1976 | Frederick | G01L 1/125 73/11.03 |
| 3,960,008 | A | * | 6/1976 | Goble | E02D 33/00 73/84 |
| 3,967,688 | A | * | 7/1976 | Inenaga | E02D 7/125 173/137 |
| 4,257,488 | A | * | 3/1981 | Schnell | E02D 13/04 173/133 |
| 4,421,180 | A | * | 12/1983 | Fleishman | B25D 11/06 173/124 |
| 4,586,366 | A | * | 5/1986 | Milberger | E02D 7/02 73/11.03 |
| 4,614,110 | A | * | 9/1986 | Osterberg | E02D 33/00 73/784 |
| 4,845,996 | A | * | 7/1989 | Bermingham | G01M 5/005 73/807 |
| 5,099,696 | A | * | 3/1992 | Yabuuchi | E02D 1/02 405/232 |
| 5,117,924 | A | * | 6/1992 | Bermingham | B25D 17/24 173/131 |
| 5,145,284 | A | * | 9/1992 | Hulett | E02D 5/24 405/227 |
| 5,256,003 | A | * | 10/1993 | Ito | E02D 3/106 405/232 |
| 5,325,702 | A | * | 7/1994 | Verstraeten | E02D 33/00 73/12.09 |
| 5,332,047 | A | * | 7/1994 | Hignite | E02D 7/08 173/1 |
| 5,410,905 | A | * | 5/1995 | Karani | G01L 5/0052 73/11.01 |
| 5,549,168 | A | * | 8/1996 | Sadler | E02D 7/18 173/129 |
| 5,581,013 | A | * | 12/1996 | Frederick | G01L 5/0052 73/11.03 |
| 5,727,639 | A | * | 3/1998 | Jeter | B25D 9/04 173/126 |
| 6,301,551 | B1 | * | 10/2001 | Piscalko | E02D 13/06 340/853.8 |
| 6,349,590 | B1 | * | 2/2002 | Wai | E02D 33/00 73/84 |
| 6,988,855 | B2 | * | 1/2006 | Fox | E02D 3/08 175/23 |
| 7,201,540 | B2 | * | 4/2007 | Ding | E02D 5/44 405/233 |
| 7,832,280 | B2 | * | 11/2010 | Hayes | G01M 99/007 73/786 |
| 8,397,583 | B2 | * | 3/2013 | Hayes | E02D 33/00 73/786 |
| 8,763,719 | B2 | * | 7/2014 | White | E02D 7/125 173/1 |
| 2003/0122434 | A1 | * | 7/2003 | Shimada | E02D 33/00 310/26 |
| 2004/0099063 | A1 | * | 5/2004 | Frederick | E02D 13/06 73/818 |
| 2005/0023014 | A1 | * | 2/2005 | Bermingham | E02D 7/02 173/2 |
| 2013/0086974 | A1 | * | 4/2013 | Rausche | G01N 3/303 73/12.01 |
| 2014/0305186 | A1 | * | 10/2014 | Touma | G01N 3/303 73/12.06 |
| 2014/0352449 | A1 | * | 12/2014 | Hale | E02D 33/00 73/786 |
| 2015/0114084 | A1 | * | 4/2015 | He | G01M 7/08 73/12.13 |
| 2018/0238013 | A1 | * | 8/2018 | Gu | E02D 33/00 |
| 2019/0226173 | A1 | * | 7/2019 | Desborough | E02D 7/02 |

FOREIGN PATENT DOCUMENTS

| | | | |
|---|---|---|---|
| CN | 204252175 U | | 4/2015 |
| CN | 106049562 | * | 10/2016 ............ E02D 33/00 |
| CN | 106049562 A | | 10/2016 |
| CN | 205839823 U | | 12/2016 |
| GB | 529328 A | | 11/1940 |
| JP | H08210957 A | | 8/1996 |

* cited by examiner

DROP HAMMER HEIGHT ADJUSTING DEVICE FOR HIGH STRAIN DETECTION OF PILE FOUNDATION

This application is a national stage application of PCT/CN2016/105034, filed on Nov. 8, 2016, which claims priority to Chinese Patent Application No. 201610564885.7, filed on Jul. 18, 2016, which is incorporated by reference for all purposes as if fully set forth herein.

FIELD OF THE INVENTION

The present invention relates to the field of constructional engineering, and more particularly to a drop hammer height adjusting device for high strain detection of a pile foundation.

DESCRIPTION OF THE RELATED ART

Foundation engineering is an important part of constructional engineering, and its quality directly affects the safety of a whole building structure and is related to the safety of people's life and property. With the increasing of building heights and complexity of building structure systems, pile foundations have become one of the major foundation forms, and the bearing capacity of a single pile is the most important technical index of the foundation piles. Currently, the main detection methods for the single pile bearing capacity include a static load test method and a high strain method. The bearing capacity of a foundation pile tested by the static load test method is visual and reliable, but there still exists many disadvantages, such as, high manpower consumption, high cost and long test time.

The high strain method for detecting the quality of a foundation pile has unique advantages, e.g., no surcharge load, less manpower, low cost, short detection time and high efficiency, and can simultaneously test two main parameters of the bearing capacity and integrity of the foundation pile, thus, the high strain method is increasingly widely applied.

The basic principle of high strain detection is as follows: a hammer is used to strike the top of a pile to generate enough relative displacement between the pile and soil to fully stimulate the resistance of the soil around the pile and the supporting force of an end of the pile, force and acceleration sensors arranged at two sides of a pile body below the top of the pile receive stress wave signals from the pile, a time-history curve between force and speed is analyzed and processed by using a stress wave theory, and thus the bearing capacity of the pile is determined and the integrity of the pile body is evaluated.

In order to produce a certain relative displacement between the pile and the soil, high energy acting on the pile is needed, and this must be realized by hammering the top of the pile using a hammer with a certain drop distance. The quality of signals and whether information in the signals is sufficient are critical to the success of a high strain test. Consequently, whether acquired signals meet requirements of the detection purpose shall be preliminarily judged according to the signal quality of every hammering. Therefore, adjusting the hammer weight and the drop distance is the key to acquisition of qualified and useful signals and success of the test. In accordance with the requirements of "Technical Code For Testing Of Building Foundation Piles" JGJ 106-2014, the hammer weight shall be not less than 2% of the characteristic value of the vertical ultimate bearing capacity of a single pile. After the hammer weight is determined, the drop distance is an important factor influencing the peak value of force and the speed of pile top. If the drop distance is too short, the energy is insufficient, and if the drop distance is too long, the peak value of force is too large, and the top of the pile is easily crushed. The drop distance is generally controlled to be 1.0-2.0 m and should not exceed 2.5 m, heavy hammer with low strike is preferable, and the hammer weight and the drop distance are selected such that the hammering penetration of the pile is 2-6 mm. If the penetration is too small, the strength of the soil is exerted insufficiently, and if the penetration degree is too large, the wave theory is not satisfied, and the actually measured waveform is distorted.

In some original high strain detection devices for foundation piles, a hammer is directly hoisted by a crane for unhooking, and the sudden release of the hammer causes that the crane jib is strongly rebounded and seriously damaged, even there is a rollover accident, and thus very serious consequences are caused. Some other high strain detection devices for foundation piles are not provided with drop hammer guiding devices, the hammer would swing to different degrees when being unhooked and is also difficult to align to the center of a pile, thus easily causing serious eccentricity of hammering and failure of detection data. The two methods do not conform to the requirements of new "Technical Code For Testing Of Building Foundation Piles" JGJ 106-2014.

Furthermore, two existing high strain detection devices for foundation piles, basically meeting the requirements of "Technical Code For Testing Of Building Foundation Piles" JGJ 106-2014, still have many disadvantages.

The first device is a sling-type gantry guide hammer carrier structure, wherein the height of a drop hammer is adjusted with the aid of a crane, by means of a steel rope and a plurality of lugs provided on an upright post at a side of a gantry. After the height of the drop hammer is adjusted, the self weight of the hammer is transferred to the gantry via the steel rope. This device has the following significant disadvantages: 1, although the steel rope has high strength, great tensile deformation is easily produced under the action of the heavy hammer due to the low elasticity modulus, and when an unhooking apparatus is used for unhooking, the sudden contraction of the steel rope causes the dramatical rebound of the hook, and thus results in the impact damages to a hook or other parts of the device and even risks to the surrounding people; 2, when the height needs to be adjusted, the height adjusting distance between the bottom of the hammer and the top of the pile needs to be manually measured, and the operation is difficult; 3, the fixed end of the steel rope must be connected with the lugs manually, and the operation is slow and inconvenient.

The second device is a clamping groove type gantry guide hammer carrier structure, wherein upright posts at two sides bear the weight of a hammer and also serve as a guiding device, and the fixation and height adjustment of the hammer are achieved by means of the clamping holes at the inner sides of the upright posts. The weight of the hammer is transferred to the upright posts at the two sides of a gantry via an unhooking apparatus. When the height needs to be adjusted, the height adjusting distance needs to be measured, and the connection between the unhooking apparatus and the gantry is relatively complicated and laborious.

SUMMARY OF THE INVENTION

The object of the present invention is to overcome the above problems in the prior art, and provides a drop hammer height adjusting device for high strain detection of a pile foundation. By means of the device, the significant disadvantages of the existing detection devices are overcome, the efficiency of obtaining qualified test signals is improved by the rapid and accurate height adjustment and test, and the precision and efficiency of high strain detection of a foundation pile are greatly improved.

In order to achieve the above purpose and technical effects, the following technical solutions are employed in the present invention.

A drop hammer height adjusting device for high strain detection of a pile foundation, comprises:

a cross beam support frame, an avoiding hole being opened in the middle of the surface of the cross beam support;

a track arranged in the avoiding hole and extending through the avoiding hole, a tooth group being arranged on each of two surfaces of the track bar, and an abutting sliding block being further provided at each side of the track;

wherein the abutting sliding block is cooperated with the tooth group to limit the position of the track bar.

Preferably, the tooth groups are arranged symmetrically on the two surfaces of the track bar.

Preferably, the tooth group is consisting of stop blocks arranged uniformly. The stop block has a first abutting inclined surface on a side surface thereof adjacent to the abutting sliding block, and the first abutting inclined surface is inclined upwards when extending towards to the track bar. The abutting sliding block has a second abutting inclined surface at a bottom thereof corresponding to the first abutting inclined surface.

Preferably, one end of the abutting sliding block is provided at a side of the surface of the track bar, and the other end of the abutting sliding block is connected with a telescopic shaft. The telescopic shaft extends through a fixed baffle, and a spring is sleeved on the telescopic shaft between the fixed baffle and the abutting sliding block. The abutting sliding block is disposed on a rail base which is arranged on the surface of the cross beam support frame.

Preferably, one end of the telescopic shaft distal to the abutting sliding block is connected with a rope, and the rope extends through a guiding device comprising a positioning plate. A threading hole is opened on the positioning plate, and a guiding wheel is arranged at a side of the positioning plate.

Preferably, the height adjusting device further comprises a detection support frame, and he cross beam support frame is fixed on the top of the detection support frame. A hammer is arranged inside the detection support frame, and the hammer is connected with the bottom of the track by an unhooking apparatus.

Preferably, two guiding parts are symmetrically provided on a side surface of the hammer. The guiding part is arranged on a guiding rod on which a plurality of U-shaped connecting plates are provided. A plurality of horizontal adjusting holes being opened on the surface of the U-shaped connecting plate which is fixed on an auxiliary upright post. The auxiliary upright post is provided on the detection support frame.

Preferably, the detection support frame comprises an upper support frame and a lower support frame, and a plurality of guiding sheets are arranged on a side surface of the top of the lower support frame.

Preferably, the track is made of steel.

As compared with the prior art, the present invention has the following advantages:

1. The rapid height adjusting device of drop hammer is designed, such that it is ensured that the hammer is adjusted upward freely and smoothly and the height of the drop hammer is rapidly fixed after the adjustment, thereby avoiding the height loss caused by untimely height fixation or the risk caused by sudden drop;

2. The intervals of track teeth can be set to be a fixed value, e.g., 100 mm, i.e., the track travels for 100 mm when advancing one tooth, and the adjusting height is calculated only by calculating the number of teeth during field test, so that manual measurement is not needed and the height adjustment is convenient and accurate;

3. The gravity of the hammer is borne by a steel track, and the steel track has axial rigidity and low tensile deformation, and can avoid the situations of strong rebound and hook throwing of a steel rope during unhooking, and thus the operation is safer;

4. the adjustable guiding device of a drop hammer is provided, such that the hammer drops steadily and collides with the foundation pile in a centering manner;

5. The adjustable guiding device of a drop hammer can adjust the horizontal distance between the two guiding rods, and thereby achieving the effective guidance for hammers with different weights;

6. The whole test is operated by only two to three persons, and the remote unhooking is achieved by means of the unhooking apparatus, and thus the safety of personnel and equipment is guaranteed.

BRIEF DESCRIPTION OF THE DRAWINGS

In order to illustrate the technical solutions in the embodiments of the present invention more clearly, the accompanying drawings used in the embodiments will be described simply. Obviously, the accompanying drawings described hereinafter only are some embodiments of the present invention, and other drawings also can be obtained without creative work for those skilled in the art.

DETAILED DESCRIPTION OF THE PREFERRED EMBODIMENTS

The technical solutions in the embodiments of the present invention will be described clearly and completely in combination with the accompanying drawings. Obviously, the described embodiments are parts of the embodiments of the present invention, instead of all of the embodiments. On the basis of the embodiments in the present invention, all other embodiments obtained by those skilled in the art without creative work belong to the protection scope of the present invention.

Figure 1:
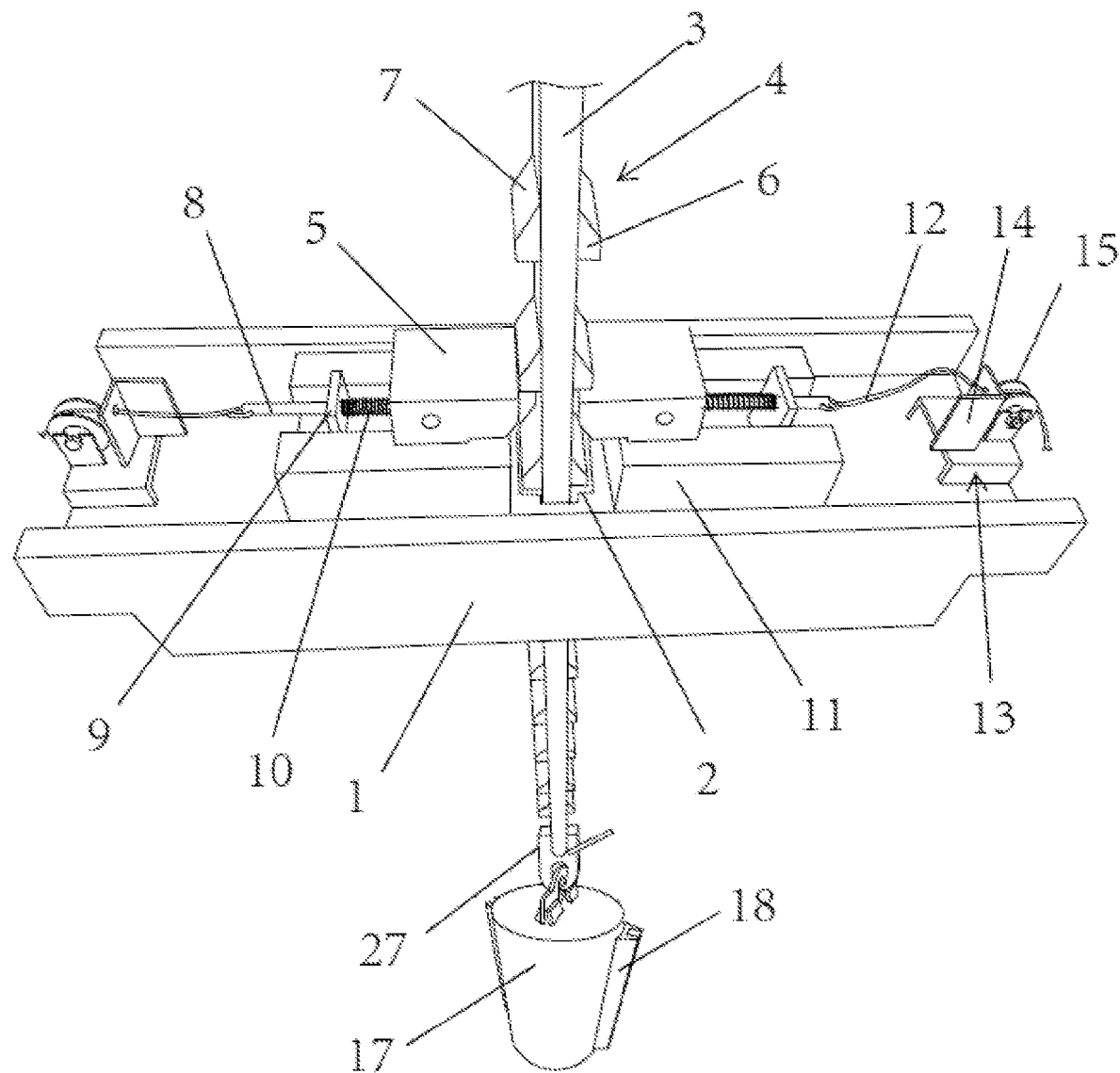
FIG. 1 is a partial schematic view of a cross beam support of the invention.
Figure 2:
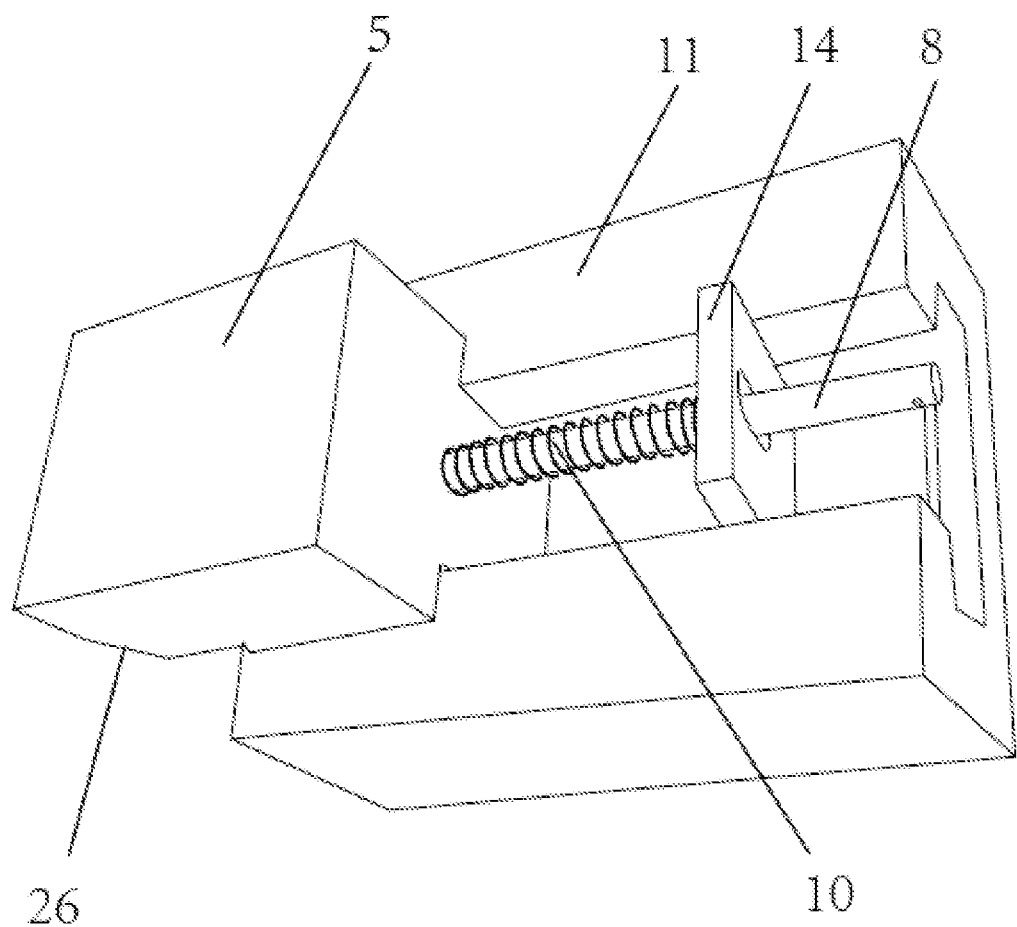
FIG. 2 is a partial schematic view of a rail base of the invention.
Figure 3:
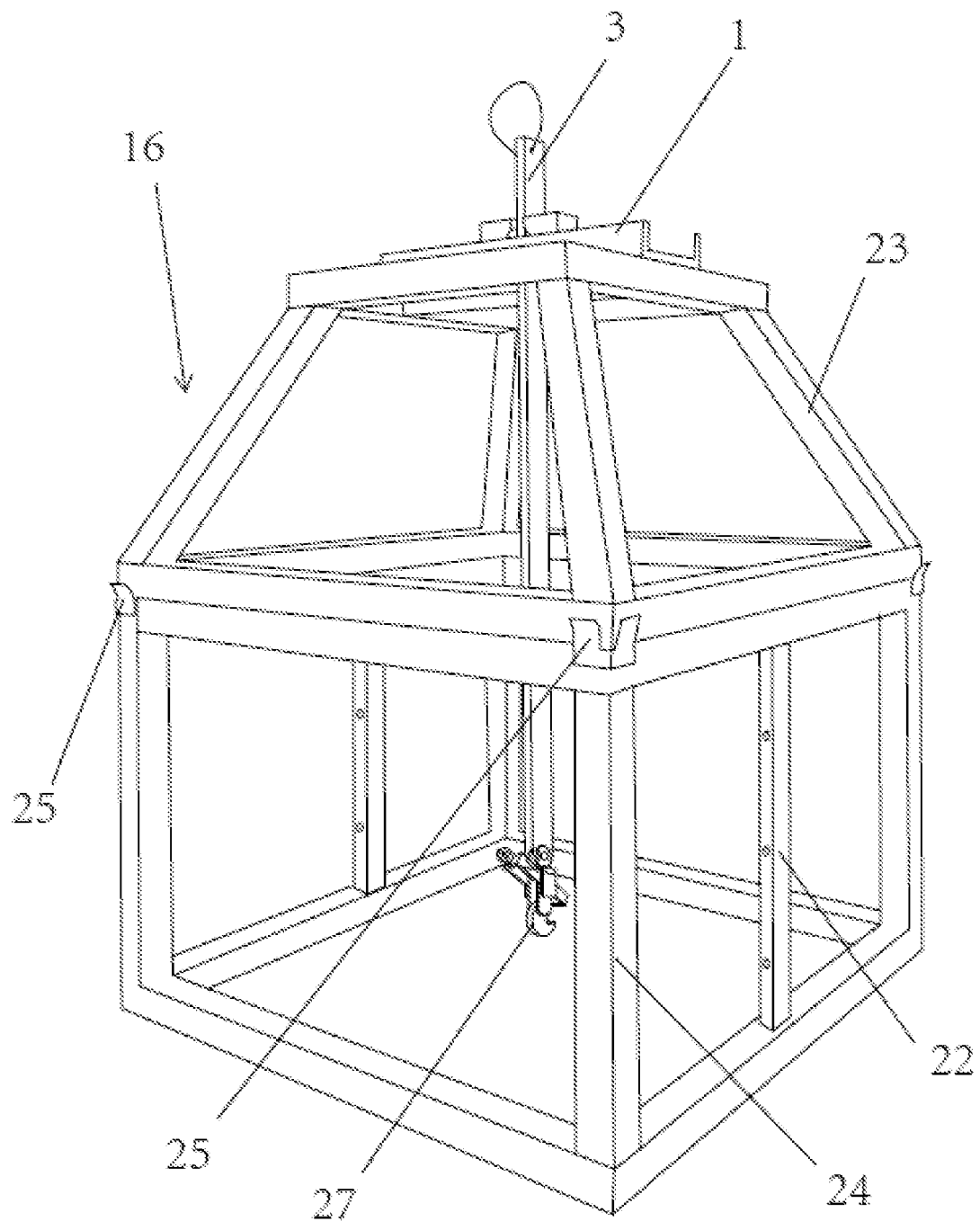
FIG. 3 is a partial schematic view of a detection support frame of the invention.
Figure 4:
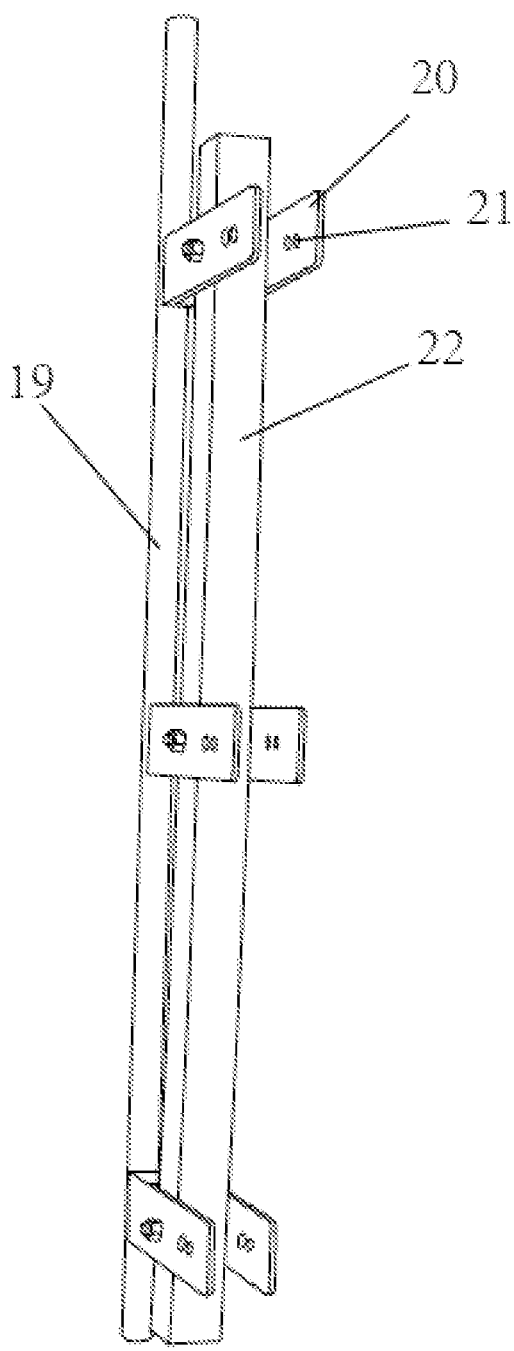
FIG. 4 is a partial schematic view of a guiding rod of the invention.

Referring to FIG. 1 to FIG. 4, a drop hammer height adjusting device for high strain detection of a pile foundation, comprises: a cross beam support frame 1, wherein an avoiding hole 2 is opened in the middle of the cross beam support; a track 3 arranged in and extends through the avoiding hole, wherein tooth groups 4 are arranged on two surfaces of the track bar, and abutting sliding blocks 5 are further arranged at two sides of the track bar, and the abutting sliding blocks are cooperated with the tooth groups to limit the position of the track bar. The avoiding hole is formed in the middle of the cross beam support platform, and the track extends through the avoiding hole and can be hung on the abutting sliding blocks via the tooth groups, so that all the weight of the track is transferred to the cross beam support frame. Thus, after the height adjustment of a drop hammer, the weight of the hammer and the track are borne by the cross beam support frame before the hammer drops.

The track is made of steel, i.e., it is a steel track. The track with this material characteristics can effectively bear the weight of the hammer, so that the device is safe and stable and has improved service life.

The tooth groups on the two surfaces of the track are arranged symmetrically, such that the weight can be shared uniformly. One end of the abutting sliding block is arranged at one side of the surface of the track bar, and the other end of the abutting sliding block is connected with a telescopic shaft 8. The telescopic shaft extends through the fixed baffle 9, a spring 10 is sleeved on the telescopic shaft between the fixed baffle and the abutting sliding block. The abutting sliding block is arranged on a rail base 11, and the rail base is arranged on the surface of the cross beam support frame. The rail base limits the abutting sliding blocks to move only along the guiding direction of a rail thereof, and the abutting sliding block is always pushed to the track by the elasticity of the spring.

The tooth group is consisting of stop blocks 6 arranged uniformly, the stop block has a first abutting inclined surface 7 on one side surface thereof adjacent to the abutting sliding block, and the first abutting inclined surface is inclined upwards when extending towards to the track bar. The abutting sliding block has a second abutting inclined surface 26 at the bottom thereof corresponding to the first abutting inclined surface. By adopting such a design, when the track is lifted up, the abutting sliding blocks move along the rail bases due to mutual abutting and cooperation of the first abutting inclined surface and the second abutting inclined surface, i.e., the rise of the track can be automatically avoided, and each stop block can enable the abutting sliding block to move once. The abutting sliding blocks can automatically reset due to the springs, such that it is ensured that the track is cooperated with the abutting sliding blocks to form a self-locking effect when the track rises to any height, and thus the device is safe and reliable.

One end of the telescopic shaft distal to the abutting sliding block is connected with a rope 12, the rope extends through a guiding device 13. The guiding device includes a positioning plate 14, and a threading hole is opened on the positioning plate for the passing of the rope to ensure that the position of the rope is fixed. A guiding wheel 15 is arranged at one side of the positioning plate. Before test, the steel track needs to be adjusted downwards, and an unhooking apparatus at the bottom of the steel track is connected with the hammer placed on the top of the pile. The abutting sliding blocks have a blocking effect due to the self-locking effect, and after the guidance of the ropes, the abutting sliding blocks can be always in an unlocking state only by pulling the ropes, and the track can thus be adjusted downwards. The cross beam support frame is arranged at a high position, the direction of the ropes can be changed by means of the guiding devices to facilitate the operation of people below, and the ropes can also be connected with a take-up motor, so that the operation can be controlled and is convenient and safe.

The device further includes a detection support frame 16, and the cross beam support frame is fixed on the top of the detection support frame. A hammer 17 is provided inside the detection support frame, and the hammer 17 is connected with the bottom of the track by an unhooking apparatus 27. The drop space and height conforming to standards are provided for the hammer. Two guiding parts 18 are symmetrically provided on the side surface of the hammer. The guiding part is disposed on a guiding rod 19, a plurality of U-shaped connecting plates 20 are arranged on the guiding rod, and a plurality of horizontal adjusting holes 21 are opened on the U-shaped connecting plate. The U-shaped connecting plates are fixed on an auxiliary upright post 22, and the auxiliary upright post is provided on the detection support frame. The guiding parts are cooperatively arranged on the guiding rods, so that the hammer can only move along the direction of the guiding rods, and thus the horizontal position of the hammer can be kept constant during dropping and will not be influenced by external factors, and the accuracy of data is improved. The guiding rods can be stably installed by means of the U-shaped connecting plates, and the distance between the two guiding rods can be adjusted by the horizontal adjusting holes on he U-shaped connecting plates, i.e., the device can adapt to the guidance of hammers having different sizes, and has good adaptability.

The detection support frame includes an upper support frame 23 and a lower support frame 24, wherein a plurality of guiding sheets 25 are arranged on the side surface of the top of the lower support frame. In practical use, during hoisting of a crane, the upper support frame will adaptively slide down along the guiding sheets, so that the relative position of the upper support frame and the lower support frame are ensured and the assembly is more convenient.

During a test, the hammer is unhooked by using the unhooking apparatus at the bottom of the steel track, the hammer drops, the unlocking part does not influence the connection part of the crane and the track bar, and any influence will not be produced on the crane, accordingly, both the personnel safety and the equipment life are guaranteed.

The abovementioned description of the disclosed embodiments enables those skilled in the art to implement or use the present invention. Multiple modifications to these embodiments are obvious to those skilled in the art, and general principles defined herein can be implemented in other embodiments without departing from the spirit or scope of the present invention. Therefore, the present invention will not be limited to theses embodiments illustrated herein, but needs to be in line with the widest scope consistent with the principles and novel features disclosed herein.

What is claimed is:

1. A drop hammer height adjusting device for high strain detection of a pile foundation, comprising:
   a cross beam support frame, an avoiding hole being opened in the middle of the cross beam support;
   a track extending through the avoiding hole, a tooth group being arranged on each of two surfaces of the track bar, and an abutting sliding block being further provided at each side of the track;
   wherein the abutting sliding block is cooperated with the tooth group to limit the position of the track bar.

2. The drop hammer height adjusting device for high strain detection of a pile foundation as claimed in claim 1, wherein the tooth groups are arranged symmetrically on the two surfaces of the track bar.

3. The drop hammer height adjusting device for high strain detection of a pile foundation as claimed in claim 1, wherein one end of the abutting sliding block is provided at a side of the track bar, the other end of the abutting sliding block is connected with a telescopic shaft, the telescopic shaft extending through a fixed baffle, a spring being sleeved on the telescopic shaft between the fixed baffle and the abutting sliding block, the abutting sliding block being disposed on a rail base which is arranged on the surface of the cross beam support frame.

4. The drop hammer height adjusting device for high strain detection of a pile foundation as claimed in claim 3, wherein the tooth group is consisting of stop blocks arranged uniformly, the stop block having a first abutting inclined surface on a side surface thereof adjacent to the abutting sliding block, and the first abutting inclined surface being inclined upwards, and the abutting sliding block having a second abutting inclined surface at a bottom thereof corresponding to the first abutting inclined surface.

5. The drop hammer height adjusting device for high strain detection of a pile foundation as claimed in claim 4, wherein one end of the telescopic shaft distal to the abutting sliding block is connected with a rope, the rope extending through a guiding device comprising a positioning plate, a threading hole being opened on the positioning plate, and a guiding wheel being arranged at a side of the positioning plate.

6. The drop hammer height adjusting device for high strain detection of a pile foundation as claimed in claim 1, wherein the height adjusting device further comprises a detection support frame on the top of which the cross beam support frame is fixed, a hammer being arranged inside the detection support frame, and the hammer being connected with the bottom of the track by an unhooking apparatus.

7. The drop hammer height adjusting device for high strain detection of a pile foundation as claimed in claim 6, wherein two guiding parts are symmetrically provided on a side surface of the hammer, the guiding part being arranged on a guiding rod on which a plurality of U-shaped connecting plates being provided, a plurality of horizontal adjusting holes being opened on the surface of the U-shaped connecting plate which is fixed on an auxiliary upright post, and the auxiliary upright post being provided on the detection support frame.

8. The drop hammer height adjusting device for high strain detection of a pile foundation as claimed in claim 6, wherein the detection support frame comprises an upper support frame and a lower support frame, and a plurality of guiding sheets being arranged on a side surface of the top of the lower support frame.

9. The drop hammer height adjusting device for high strain detection of a pile foundation as claimed in claim 1, wherein the track is made of steel.

* * * * *